(12) United States Patent
Bhullar et al.

(10) Patent No.: US 6,814,843 B1
(45) Date of Patent: Nov. 9, 2004

(54) BIOSENSOR

(75) Inventors: Raghbir S. Bhullar, Indianapolis, IN (US); Douglas P. Walling, Indianapolis, IN (US); Brian S. Hill, Avon, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 118 days.

(21) Appl. No.: 09/704,235

(22) Filed: Nov. 1, 2000

(51) Int. Cl.$^7$ .................... G01N 27/327; B32B 31/00
(52) U.S. Cl. ...................... 204/403.01; 204/403.14; 156/292
(58) Field of Search ................ 204/403.01, 403.14, 204/416; 422/58; 156/292, 291, 252

(56) References Cited

U.S. PATENT DOCUMENTS

| | | | |
|---|---|---|---|
| 4,963,814 A | 10/1990 | Parks et al. | |
| 4,999,582 A | 3/1991 | Parks et al. | |
| 4,999,632 A | 3/1991 | Parks | |
| 4,477,575 A | 4/1992 | Vogel et al. | |
| 5,141,868 A | 8/1992 | Shanks et al. | |
| 5,243,516 A | 9/1993 | White | |
| 5,288,636 A | 2/1994 | Pollmann et al. | |
| 5,336,388 A | 8/1994 | Leader et al. | |
| 5,352,351 A | 10/1994 | White et al. | |
| 5,366,609 A | 11/1994 | White et al. | |
| 5,385,846 A | 1/1995 | Kuhn et al. | |
| 5,405,511 A | 4/1995 | White et al. | |
| 5,413,690 A | 5/1995 | Kost et al. | |
| 5,438,271 A | 8/1995 | White et al. | |
| 5,576,073 A | 11/1996 | Kickelhain | |
| 5,593,739 A | 1/1997 | Kickelhain | |
| 5,759,364 A | 6/1998 | Charlton et al. | |
| 5,762,770 A | 6/1998 | Pritchard et al. | |
| 5,798,031 A | 8/1998 | Charlton et al. | |
| 5,997,817 A | 12/1999 | Crismore et al. | |
| 6,004,441 A | 12/1999 | Fujiwara et al. | |
| 6,110,696 A | 8/2000 | Brown et al. | 435/7.6 |
| 6,125,292 A | * | 9/2000 | Uenoyama et al. .... 204/403.14 |
| 6,174,420 B1 | * | 1/2001 | Hodges et al. ......... 204/403.11 |
| 6,319,719 B1 | * | 11/2001 | Bhullar et al. ............. 422/101 |
| 6,326,160 B1 | * | 12/2001 | Dunn et al. ................ 204/400 |

FOREIGN PATENT DOCUMENTS

| | | |
|---|---|---|
| EP | 0 287 883 A1 | 10/1988 |
| EP | 0 964 059 | 12/1999 |
| EP | 1 098 000 | 5/2001 |
| JP | 11 087384 | 3/1999 |
| WO | WO 00/73778 | 12/2000 |
| WO | WO 00/73785 | 12/2000 |

OTHER PUBLICATIONS

Petrie (pp. 279–284 of Handbook of Adhesives and Sealants, McGraw–Hill, 2000).*
LPKF MicrolineLaser II, LPKF Laser & Electronics AG; LPKF; Art.–Nr. 107645–2 (01/00) (2pp.).
Microline Solutions, LPKF Laser & Electronics AG; LPKF; art.–Nr. 107658–1 (01/00) (4pp.)

* cited by examiner

*Primary Examiner*—Alex Noguerola
(74) *Attorney, Agent, or Firm*—Jill L. Woodburn

(57) ABSTRACT

A biosensor is provided that comprises a substrate, a reagent positioned on the substrate, and a cover including a top side and a generally flat bottom side. The bottom side is coupled to the substrate to define a sealed portion and an unsealed portion. The unsealed portion cooperates with the substrate to define a channel extending across the reagent.

35 Claims, 4 Drawing Sheets

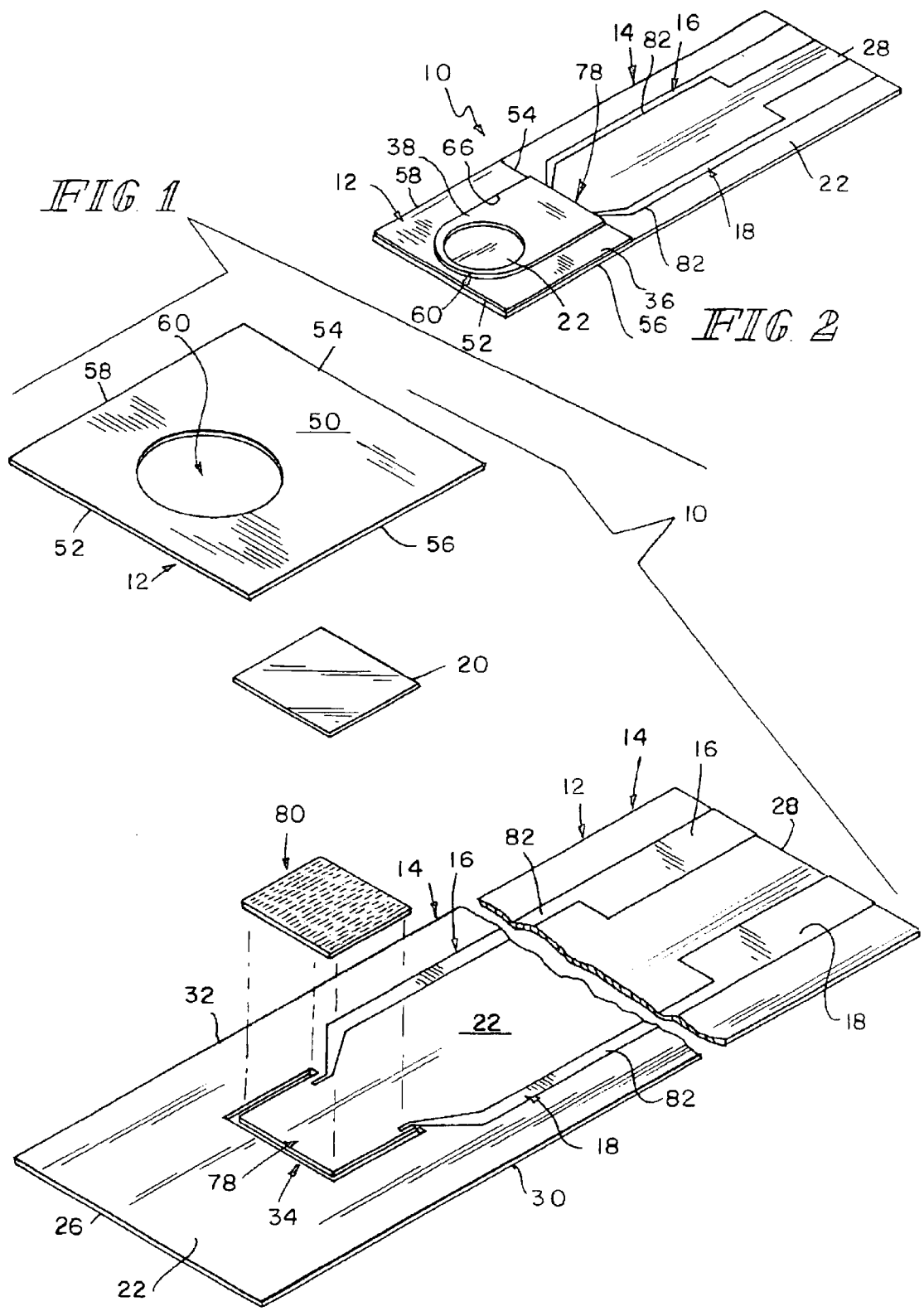

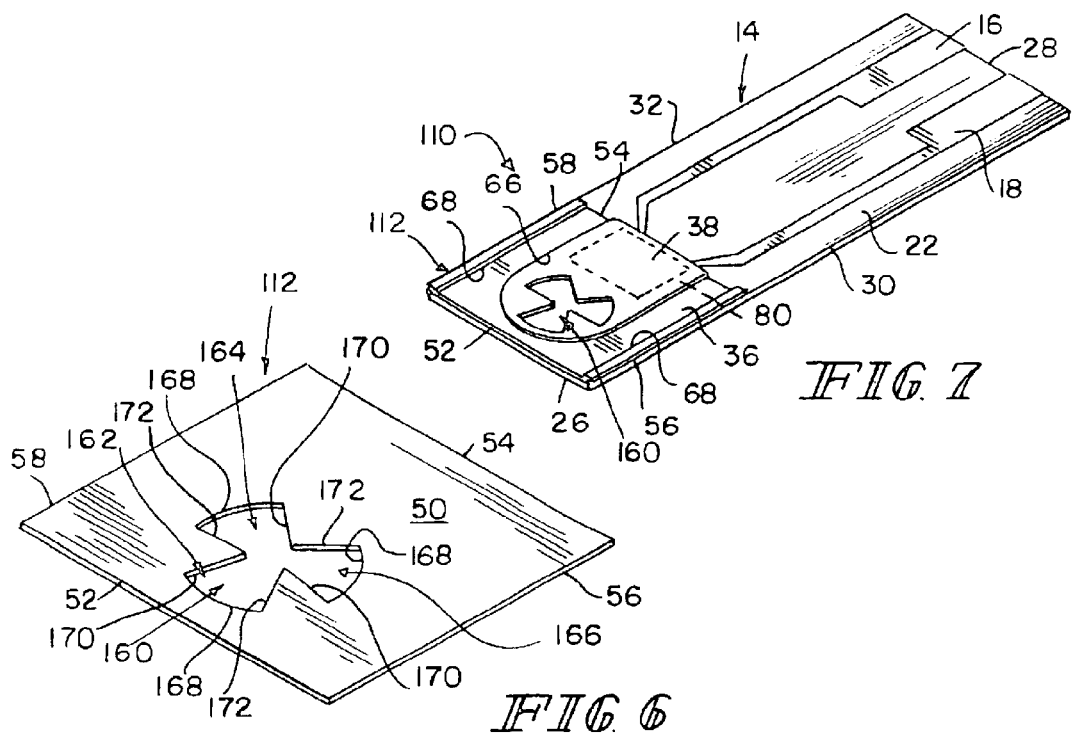
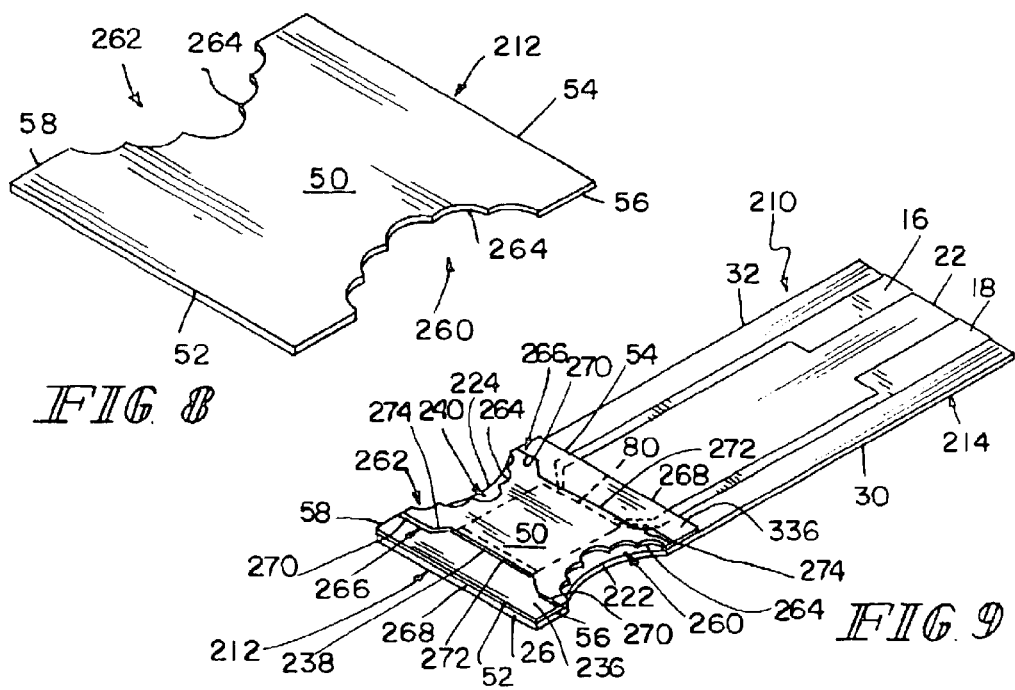

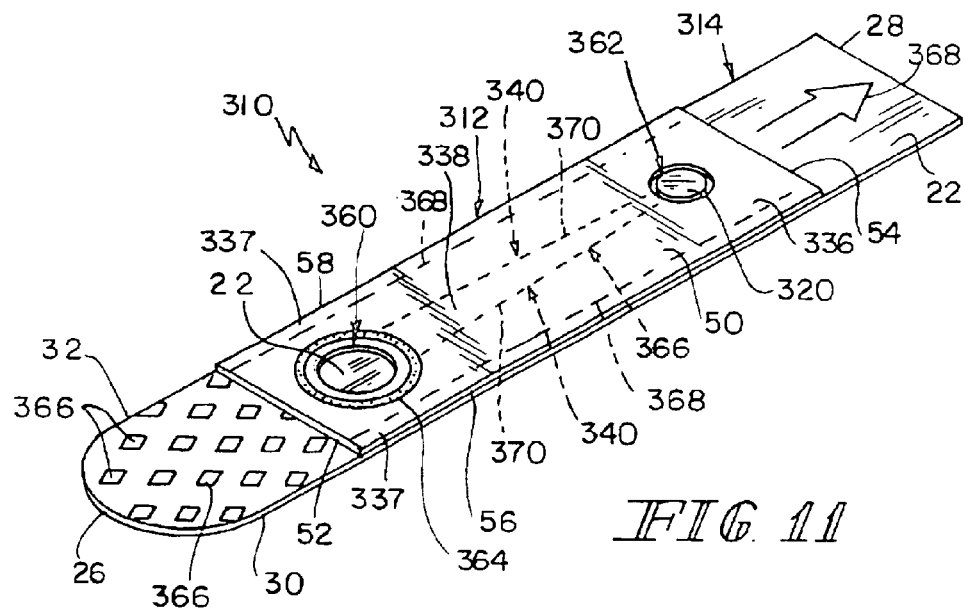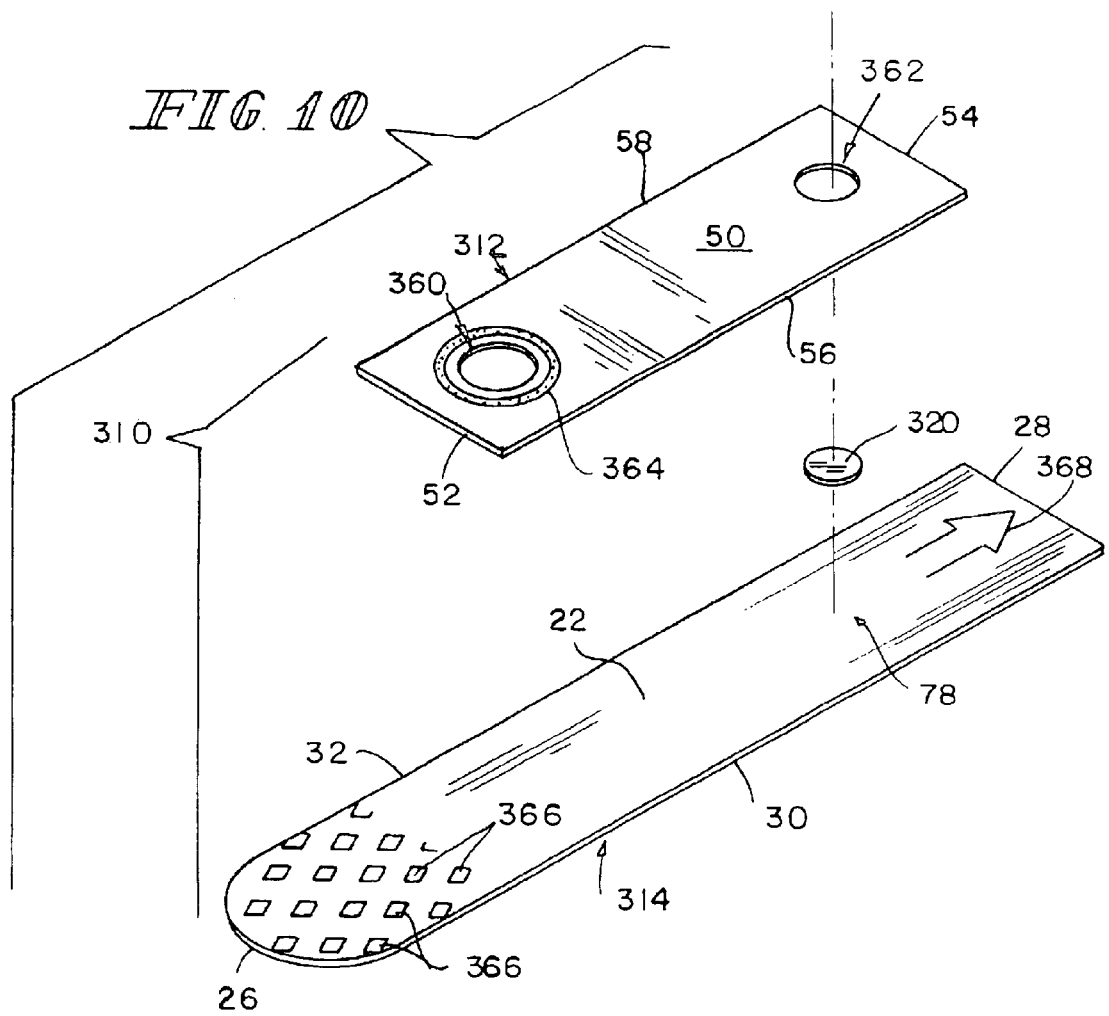

US 6,814,843 B1

BIOSENSOR

FIELD OF THE INVENTION

The present invention relates to a biosensor for use in determining the concentration of an analyte in a sample.

BACKGROUND AND SUMMARY OF THE INVENTION

Electrochemical biosensors are known. They have been used to determine the concentration of various analytes from biological samples, particularly from blood. Biosensors are described in U.S. Pat. Nos. 5,288,636; 5,413,690; 5,762,770; 5,798,031; and 5,997,817, the disclosure of each of which are expressly incorporated herein by reference.

It is known to emboss a lid formed of a deformable material to form a concave area that acts as a capillary space into which a fluid test sample can be drawn. See, for example, U.S. Pat. No. 5,759,364. It is also known to form a capillary gap between opposing surface areas spaced apart by a spacer layer. See, for example, European Patent Appln. 0 287 883 to Miles Inc. and U.S. Pat. No. 5,141,868.

According to the present invention, a biosensor is provided that forms a capillary channel between a cover and substrate, without the aid of a spacer or the additional manufacturing step of embossing either the cover or the substrate. The biosensor comprises a substrate, a reagent positioned on the substrate, and a cover including a top side and a generally flat bottom side. The bottom side is coupled to the substrate to define a sealed portion and an unsealed portion. The unsealed portion cooperates with the substrate to define a channel extending across the reagent.

In addition, according to the invention a biosensor is provided that comprises a substrate, a reagent positioned on the substrate, and a cover having a top side and a generally flat bottom side, and an opening extending between the top and bottom sides. The bottom side is coupled to the substrate to define a sealed portion and an unsealed portion. The unsealed portion cooperates with the substrate to define a channel extending between the opening and the reagent.

Further, according to the invention a method of forming a biosensor having a capillary channel is provided. The method comprises the steps of providing a substrate, providing a cover having a top surface and a bottom surface, placing a thermoset adhesive on the bottom surface of the cover, placing the adhesive-coated bottom surface on the substrate, and heating portions of the thermoset adhesive to couple the bottom side to the substrate to define a sealed portion and an unsealed portion. The unsealed portion cooperates with the substrate to define a channel extending across the reagent.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 1 is an exploded assembly view of a biosensor in accordance with the present invention, showing the biosensor including a substrate, a reagent, and a cover formed to cover the reagent and substrate;

FIG. 2 is a perspective view of the assembled biosensor of FIG. 1;

FIG. 6 is a perspective view of a cover;

FIG. 7 is a perspective view of a biosensor in accordance with another aspect of the present invention, the biosensor including the cover of FIG. 6;

FIG. 8 is a perspective view of another cover;

FIG. 9 is a perspective view of a biosensor in accordance with another aspect of the present invention, the biosensor including the cover of FIG. 8;

FIG. 10 is an exploded assembly view of a biosensor in accordance with another aspect of the present invention showing the biosensor including a substrate, a regent, and a cover having two spaced-apart openings; and FIG. 11 is a perspective view of the assembled biosensor of FIG. 10.

DETAILED DESCRIPTION OF THE DRAWINGS

Figure 3:
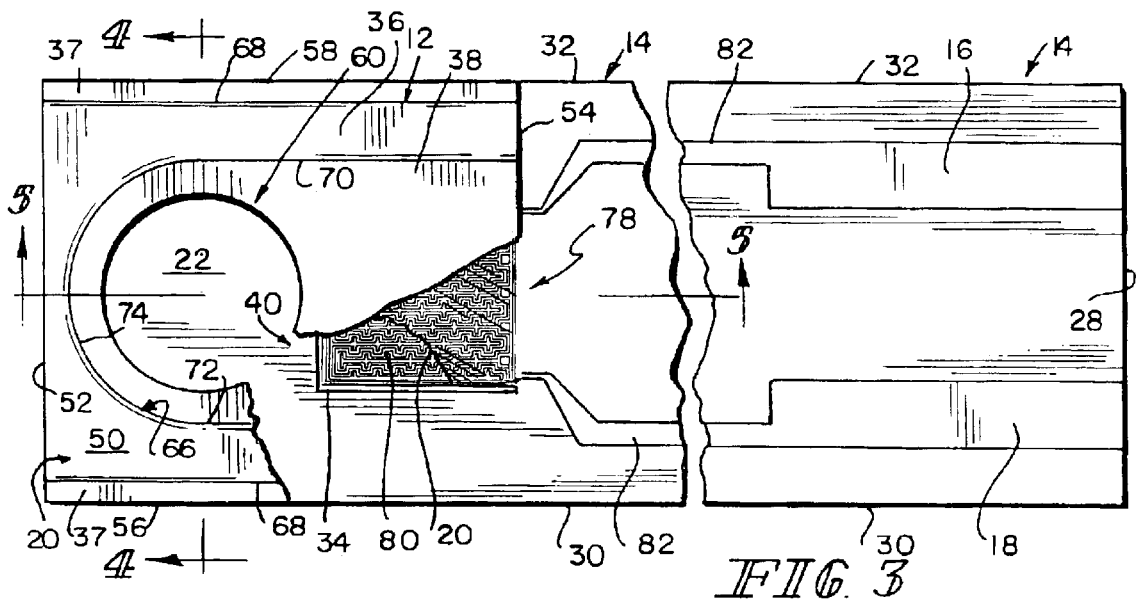
FIG. 3 is a plan view of the biosensor of FIG. 2 with portions broken away.

The present invention relates to a biosensor that enables a capillary channel to be produced at low cost with commercially available technologies. The biosensor of the present invention includes a cover and a substrate, both of which are formed without a predefined channel and a reagent supported by the substrate. The cover is sealed to the substrate in a particular pattern leaving an unsealed portion, which extends between an opening and a predefined reaction area where diagnostic testing for a particular analyte occurs. The cover and substrate inherently do not lie perfectly flat against one another, and therefore the capillary channel is created by default between unsealed portions of the cover and the substrate. The biosensor of the present invention takes advantage of surface irregularities of the cover and the substrate and the thickness of the reagent to form the capillary channel to move a liquid sample across the substrate and toward the reaction site. Various aspects of the invention are presented in FIGS. 1-11, which are not drawn to scale and wherein like components in the several views are numbered alike.

FIGS. 1-5 illustrate an aspect of the invention in the form of an electrochemical biosensor 10 having a cover 12, a bottom substrate 14, electrically conductive tracks 16, 18 and a reagent 20 extending over a portion of tracks 16, 18. Biosensor 10 is preferably rectangular in shape. It is appreciated, however, that biosensor 10 can assume any number of shapes in accordance with this disclosure. Biosensor 10 is preferably produced from rolls of material, however, it is understood that biosensor 10 can be constructed from individual sheets in accordance with this disclosure. Thus, the selection of materials for the construction of biosensor 10 necessitates the use of materials that are sufficiently flexible for roll processing, but which are still rigid enough to give a useful stiffness to finished biosensor 10.

Cover 12 of biosensor 10 includes a first surface 48 facing substrate 14 and an opposite second surface 50. See FIGS. 1 and/or 4. In addition, cover 12 has opposite ends 52, 54 and edges 56, 58 extending between ends 52, 54. An opening 60 extends between first and second surfaces 48, 50 as shown in FIG. 1. When cover 12 is coupled to substrate 14, opening 60 is off-set from reagent 20. See FIG. 3. It is appreciated, however, that opening 60 can be located in a number of locations in accordance with this disclosure. Preferably, cover 12 is 3 mil thick ST505 MYLAR® polyester film commercially available from E. I. DuPont de Nemours, Wilmington, Del.

Additionally, while not illustrated, first surface 48 of cover 12 is coated with an adhesive such as a thermoset adhesive. A non-limiting example of such an adhesive is a blend of item #38-8569 (95% wt./wt. polyurethane and 5% wt./wt. isocyanate) and item #38-8668 (7% wt./wt. Triton X-100 detergent and 1–2% wt./wt. fumed silica), both commercially available from National Starch& Chemical, a Member of ICI Group, Bridgewater, N.J. It is appreciated that cover 12 may be coupled to bottom substrate 14 using a wide variety of commercially available adhesives or with welding (heat or ultrasonic) in accordance with this disclosure. It is also appreciated that second surface 50 of cover 12 may be printed with, for example, product labeling or instructions for use in accordance with this disclosure.

As shown in FIG. 3, since cover 12 lacks a pre-defined channel, it lies in a generally flat position upon substrate 14. Since cover 12 and substrate 14 inherently do not lie perfectly flat against one another, when portions 36 of cover 12 are coupled to substrate 14, small gaps/channels 40, 62, 64 are created by default between unsealed portions 38 and substrate 14. It is believed that these gaps/channels 40, 62, 64 are created due to surface irregularities of cover 12 and substrate 14 as well as due to the presence of reagent. See the enlarged views of FIGS. 4 and 5. Biosensor 10 takes advantage of these surface irregularities as well as the thickness of the reagent to form capillary channel 40 to move small volumes of blood across substrate 14 and toward reagent 20.

Figure 4:
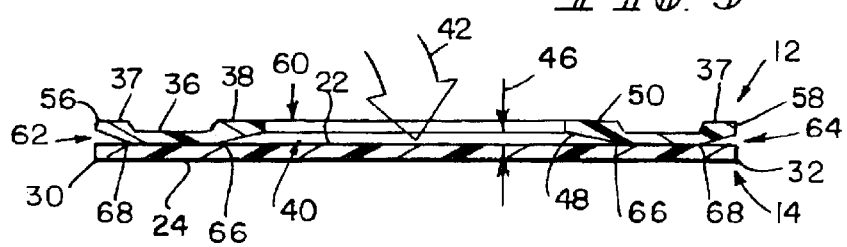
FIG. 4 is a an enlarged cross-sectional view taken along lines 4—4 of FIG. 3.
Figure 5:
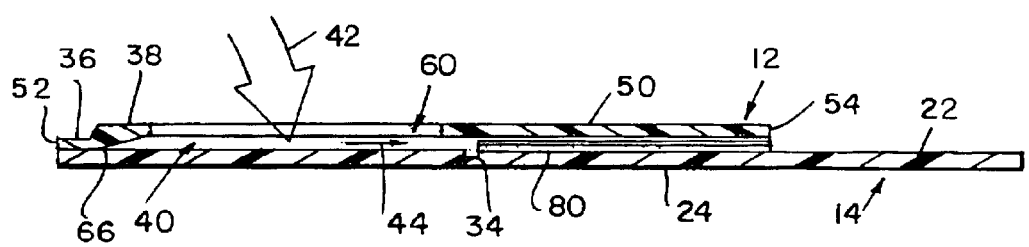
FIG. 5 is an enlarged cross-sectional view taken along lines 5—5 of FIG. 3.

Referring now to FIGS. 3 and 4, cover 12 is coupled to substrate 14 so that sealed portion 36 has an interior border 66 and an exterior border 68. Interior border 66 is generally U-shaped and includes opposite legs 70, 72 and a curved end 74 extending between legs 70, 72. Exterior borders 68 are generally linear and lie spaced-apart from edges 56, 58 to form unsealed portions 37 of cover 12. Unsealed portions 37 of cover 12 form gaps 62, 64 between cover 12 and substrate 14. Although sealed portion 36 and unsealed portions 37, 38 are clearly distinguishable from one another in the views of FIGS. 2, and 3, it is appreciated that portions 36, 37, 38 will not always be visible to a user. For example, portions 36, 37, 38 may not be visible to a user when cover 12 is opaque. Portion 36 may, however, be visible to a user of biosensor 10 during use when cover 12 is transparent and the liquid sample being tested is colored. In addition, it is appreciated that the shape and size of borders 66, 68 can vary in accordance with this disclosure.

Unsealed portion 36 of cover 12 is positioned within border 66 and cooperates with substrate 14 to form capillary channel 40 between cover 12 and substrate 14. Referring again to the enlarged cross-sectional view of FIG. 4, channel 40 is defined by cover 12, substrate 14, and interior border 66 of sealed portion 36. In addition, channel 40 is aligned with opening 60 and extends to end 54 of cover 12. See FIGS. 3 and 5. Channel 40 has a height, as shown by arrows 46 in FIG. 4, of about 1 $\mu$m to about 60 $\mu$m, preferably 2 $\mu$m to about 30 $\mu$m, and most preferably about 5 $\mu$m to about 15 $\mu$m. In addition, the width of channel 40 between opposite legs 70, 72 of exterior border 66 is about 1 mm to about 4 mm, preferably 2 mm to about 3 mm, most preferably about 2.5 mm to about 2.75 mm. It is appreciated that since the channel is not pre-formed in either cover 12 or substrate 14, the height of channel will vary depending upon surface irregularities that are inherent to the material from which cover 12 and substrate 14 are formed, the thickness of reagent, and the consistency of the applied adhesive (if present).

Bottom substrate 14 of biosensor 10 includes a first surface 22 that supports conductive tracks 16, 18 and an opposite second surface 24. See FIGS. 4-5. In addition, substrate 14 has opposite ends 26, 28 and edges 30, 32 extending between ends 26, 28. See FIG. 1. Bottom substrate 14 may be constructed from a wide variety of insulative materials. Non-limiting examples of insulative materials that provide desirable electrical and structural properties include glass, ceramics vinyl polymers, polyimides, polyesters, and styrenics. Preferably, bottom substrate 14 is a flexible polymer, such as a polyester or polyimide. A non-limiting example of a suitable material is 5 mil thick KALADEX®, a polyethylene naphthalate film commercially available from E. I. DuPont de Nemours, Wilmington, Del., which is coated with gold with gold by LPKF Laser Electronic GmbH, of Garbsen, Germany.

Biosensors 10 in accordance with the present invention are each formed to include a pre-defined reaction area 78 where the sensing takes place. When the biosensor is electrochemical, the pre-defined area is an electrochemical area that is located on a portion of the electrodes 16, 18. Referring now to FIG. 1, biosensor 10 includes an electrochemical reaction area 78, which is defined as the area of electrodes where reagent 20 is located. A recess 34 is formed in substrate 14 of biosensor 10 and extends about a portion of area 78. It is appreciated that recess 34 can take on any number of shapes and sizes in accordance with this disclosure. The method of forming recess 34 in substrate 14 is not limited. For example, the recess may be formed by indenting, embossing, etching (e.g., using photoligographic methods or laser removal of a portion of the base material), or otherwise deforming or removing a portion of the base material. For a further description of recesses, see U.S. Patent Application No. Not Yet Available entitled Biosensor to Bhullar et al., which was filed in the U.S. Patent and Trademark Office on Oct. 6, 2000, the disclosure of which is expressly incorporated herein by reference.

As shown in FIG. 1, electrically conductive tracks 16, 18 are created or isolated onto first surface 22 of bottom substrate 14. Tracks 16, 18 represent the electrodes of biosensor 10. As used herein, the phrase "electrode set" is a set of at least two electrodes, for example 2 to 200, or 3 to 20, electrodes. These electrodes may, for example, be a working electrode and a reference electrode. Tracks 16, 18 cooperate to form an interdigitated electrode array 80 positioned within the periphery of recess 34 and leads 82 that extend from array 80 toward end 28.

Tracks 16, 18 are constructed from electrically-conductive materials. Non-limiting examples of electrically-conductive materials include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, tracks include gold, platinum, palladium, iridium, or alloys of these metals, since such noble metals and their alloys are unreactive in biological systems. Most preferably, track 16 is a working electrode made of gold, and track 18 is an auxiliary electrode that is also made of gold and is substantially the same size as the working electrode.

Tracks 16, 18 are formed or created or isolated from the rest of the electrically-conductive surface by laser ablation.

Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE", the disclosure of which is expressly incorporated herein by reference. Tracks 16, 18 are preferably created by removing the electrically conductive material from an area extending around the electrodes.

Tracks 16, 18 are preferably created by removing the electrically-conductive material from an area extending around the electrodes. Therefore, tracks 16, 18 are isolated from the rest of the electrically-conductive material on bottom substrate 14 by a gap having a width of about 25 $\mu$m to about 500 $\mu$m, preferably about 100 $\mu$m to about 200 $\mu$m. Alternatively, it is appreciated that tracks 16, 18 may be created by laser ablation alone on bottom substrate 14. Further, tracks 16, 18 may be laminated, screen-printed, or formed by photolithography in accordance with this disclosure.

Multi-electrode arrangements are also possible in accordance with this disclosure. For example, it is contemplated to form a biosensor 10 that includes an additional electrically conductive track (not shown). In a three-electrode arrangement, the first track is a working electrode, the second is a counter electrode, and the third electrode is a reference electrode. It is also appreciated that a three-electrode arrangement is possible where tracks are working electrodes and a third electrode is provided as an auxiliary or reference electrode in accordance with this disclosure. It is appreciated that the number of tracks, as well as the spacing between tracks in array 80 may vary in accordance with this disclosure and that a number of arrays may be formed as will be appreciated by one of skill in the art.

Reagent 20 provides electrochemical probes for specific analytes and is applied onto bottom substrate 14 such that reagent 20 covers array 80. A liquid reagent 20 is placed onto array 80. The choice of specific reagent 20 depends on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100–900 kilo Daltons), 3.3 mg NATROSOL 244M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is incorporated herein by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a crystalline material (Avicel RC-591F—a blend of 88% crystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is incorporated herein by reference.

Non-limiting examples of enzymes and mediators that may be used in measuring particular analytes in sensor 10 of the present invention are listed below in Table 1.

TABLE 1

| Analyte | Enzymes | Mediator (Oxidized Form) | Additional Mediator |
|---------|---------|--------------------------|---------------------|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensor 10 in accordance with this disclosure.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in cassette magazine, or packed in a blister packaging.

Biosensor 10 is used in conjunction with the following:
1. a power source in electrical connection with the electrodes and capable of supplying an electrical potential difference between the electrodes sufficient to cause diffusion limited electro-oxidation of the reduced form of the mediator at the surface of the working electrode; and
2. a meter in electrical connection with the electrodes and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are expressly incorporated herein by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, whole blood is assayed with this invention.

After reaction is complete, a power source (e.g., a battery) applies a potential difference between electrodes. When the potential difference is applied, the amount of oxidized form of the mediator at the auxiliary electrode and the potential difference must be sufficient to cause diffusion-limited electro-oxidation of the reduced form of the mediator at the surface of the working electrode. A current measuring meter (not shown) measures the diffusion-limited current generated by the oxidation of the reduced form of the mediator at the surface of the working electrode. The measured current may be accurately correlated to the concentration of the analyte in sample when the following requirements are satisfied:
1. The rate of oxidation of the reduced form of the mediator is governed by the rate of diffusion of the reduced form of the mediator to the surface of the working electrode.
2. The current produced is limited by the oxidation of reduced form of the mediator at the surface of the working electrode.

To manufacture biosensor 10 a roll of metallized film is fed through guide rolls into an ablation/washing and drying station. A laser system capable of ablating substrate 14 is known to those of ordinary skill in the art. Non-limiting examples of which include excimer lasers, with the pattern of ablation controlled by mirrors, lenses, and masks. A non-limiting example of such a system is the LPX-300 or LPX-200 both commercially available from LPKF Laser Electronic GmbH, of Garbsen, Germany.

In the laser ablator, the metallic layer of the metallized film is ablated in a predetermined pattern, to form an electrode set ribbon. The metallized film is further ablated, after the electrode pattern is formed to create recess 34 positioned adjacent to the pattern. The ribbon is then passed through more guide rolls, with a tension loop and through an optional optical or electrical inspection system. This inspection system is used for quality control in order to check for defects.

Reagent 20 is compounded and applied in a liquid form to the center of area 78 at a dispensing and drying station. Reagent application techniques are well known to one of ordinary skill in the art as described in U.S. Pat. No. 5,762,770, the disclosure of which is incorporated herein by reference. It is appreciated that reagent may be applied to area 78 in a liquid or other form and dried or semi-dried onto the center of area 78 in accordance with this disclosure.

In addition, a thermoset adhesive coated roll of cover material is fed into a slitting and punching station to punch opening 60 in cover material. The cover material is then slit into the appropriate width for a row of biosensors 10. The adhesive-coated cover material is fed into a sensor assembly station along with the reagent-coated bottom substrate.

In the sensor assembly station, the thermoset adhesive-coated side of the cover material is placed on substrate 14 so that the cover material covers array 80. Next, a hot iron (not shown) of appropriate desirable channel shape and size is placed upon surface 50 of cover material to heat seal sealed portion 36 to substrate 14. Since iron does not heat the thermoset adhesive that is adjacent to unsealed portion 38, channel 40 is formed by default between unsealed portion 38 of cover 12 and substrate 14. The sides of channel 40 are defined by interior border 66 of sealed portion 36. Once channel 40 is formed, the assembled material is fed into a sensor cutting and packing station to form individual biosensors 10, which are sorted and packed into vials, each closed with a stopper, to give packaged sensor strips.

In use, a user of biosensor 10 places a finger over opening 60. The liquid blood sample flows through opening 60 as shown by arrow 42 in FIGS. 4-5. Capillary forces pull the liquid sample from opening 60 through channel 40 toward end 54 of cover 12 as shown by arrow 44. The liquid blood sample dissolves reagent 20 and engages electrode array 80, where the electrochemical reaction takes place. The processes and products described above include disposable biosensor, especially for use in diagnostic devices. Also included, however, are electrochemical sensors for non-diagnostic uses, such as measuring an analyte in any biological, environmental, or other sample. As discussed above, biosensor 10 can be manufactured in a variety of shapes and sizes.

A biosensor 10 is provided in accordance with another aspect of this invention and is illustrated in FIG. 7. Biosensor 110 is constructed of materials similar to biosensor 10 and is formed to include a cover 112 that has an opening 160 that is designed to aid in the spreading of the liquid sample in channel 40. See FIG. 6. Opening 160 of cover 112 includes three generally tri-angular segments 162, 164, 166 that are each defined by a concave outer segment 168 and side walls 170, 172 that converge toward outer segment 168. Referring now to FIG. 7, opening 160 is spaced-apart from electrode array 80 when biosensor 110 is assembled. It is appreciated, however, that opening 160 can be located in a number of locations in accordance with this disclosure.

Like cover 12, cover 112 and substrate 14 are sealed together in a predetermined pattern such that sealed portion 36 cooperates with unsealed portion 38 to define, by default, capillary channel 40 that extends between opening 160 and end 54 of cover 112. Additionally, as shown in FIGS. 7, sealed portion 136 does not extend to edges 56, 58 of cover 112. Therefore, unsealed gaps similar to gaps 62, 64, as shown in FIG. 4, exist between edges 30, 56 and edges 32, 58 respectively. Sealed portion 36 of cover 112 is coupled to substrate 14 by an adhesive such as a thermoset adhesive as described above with reference to biosensor 10. It is appreciated that cover 112 may be coupled to bottom substrate 14 using a wide variety of commercially available adhesives or with welding (heat or ultrasonic) in accordance with this disclosure.

Biosensor 110 is constructed and used in a manner similar to biosensor 10 as described above, except that opening 160 is shaped differently than opening 60. In addition, the height and width of the channel formed between unsealed portion 38 of cover 112 and substrate 14 is similar to that of biosensor 10 as described above.

As shown in FIG. 9, a side-dose biosensor 210 is provided in accordance with another aspect of this invention. Biosensor 210 is constructed of materials similar to biosensor 10 and includes a cover 212, a bottom substrate 214, and electrically conductive tracks 16, 18. Referring now to FIG. 8, cover 212 of biosensor 210 includes openings 260, 262 formed in edges 56, 58 respectively. Each opening 260, 262 includes a disrupted concave surface 262. When cover 212 is coupled to substrate 214, as shown in FIG. 9, openings 260, 262 are spaced-apart from electrode array 80. It is appreciated, however, that openings 260, 262 can be located in a number of locations in accordance with this disclosure.

Edges 30, 32 of bottom substrate 214 have generally concave notches 222, 224 adjacent to end 26 in order to accommodate a user's finger. Notches 222, 224 are positioned in general alignment with openings 260, 262 in cover 212 upon assembly of biosensor 210. It is appreciated that biosensor 210 may be formed without notches, or that notches may take on any number of shapes in accordance with this disclosure.

As shown in FIG. 9, cover 212 and substrate 214 are sealed together in a predetermined pattern to form spaced-apart sealed portions 236 that extend between edges 56, 58. Sealed portions 236 each have an interior border 266 and an exterior border 268. Sealed portion 236 of cover 212 is coupled to substrate 214 by an adhesive such as a thermoset adhesive as described above with reference to biosensor 10. It is appreciated that cover 212 may be coupled to bottom substrate 214 using a wide variety of commercially available adhesives or with welding (heat or ultrasonic) in accordance with this disclosure.

Each interior border 266 of sealed portion 336 has opposite outer segments 270, an inner segment 272, and transition segments 274 that converge from each outer segment 270 toward inner segment 272. Therefore, by default, an unsealed portion 238 that is positioned between sealed portions 236 defines a capillary channel 240 to between notches 260, 262 of substrate 214 and openings 260, 262 of cover 212. The height of channel 240 is similar to that of channels 40, 140 as described above with reference to biosensor 10, 110. The width of channel 240, however, varies as it converges from outer segments 270 toward inner segments 272. The width of channel between outer segments 270 of channel 240 is about 100 $\mu$m to about 5000 $\mu$m, preferably 1000 $\mu$m to about 4000 $\mu$m, most preferably about 1500 $\mu$m to about 3000 $\mu$m. The width of channel 240 between inner segments 272 is about 50 $\mu$m to about 4000 $\mu$m, preferably about 500 $\mu$m to about 3000 $\mu$m, most preferably about 1000 $\mu$m to about 2500 $\mu$m.

To manufacture biosensor 210 a roll of metallized film is fed through guide rolls into an ablation/washing and drying station as described above with reference to biosensor 10 to form an electrode set ribbon and to create recess 34 positioned adjacent to the pattern. Thermoset adhesive coated rolls of cover material are fed into a slitting and punching station where openings 260, 262 are punched in cover material. In addition, the adhesive-coated cover material is slit into the appropriate width for a row of biosensors 10. Next, the adhesive-coated cover material is fed into a sensor assembly station along with the reagent-coated bottom substrate.

In the sensor assembly station, the thermoset adhesive-coated side of the cover material is placed on the substrate material so that the notches 222, 224 are aligned with openings 260, 262 as shown in FIG. 9. Next, spaced-apart irons (not shown) of appropriate desirable channel shape and size are placed upon surface 50 of cover material to couple sealed portion 236 to substrate 214. Again, unsealed portion 238 is not exposed to the heat of the iron, and therefore is not coupled to bottom substrate 214. Therefore, channel 240 is formed between cover 212 and substrate 214 and formed to extend between openings 260, 262. Once channel 240 is formed, the assembled material is fed into a sensor cutting and packing station where the material is cut to form individual biosensors 210, which are sorted and packed into vials, each closed with a stopper, to give packaged sensor strips.

Referring now to FIGS. 10-11, a biosensor 310 is formed in accordance with the present invention. Biosensor 310 has a cover 312, a bottom substrate 314, and a reagent 320. It is appreciated, however, that biosensor 310 can assume any number of shapes in accordance with this disclosure. Biosensor 310 is preferably produced from materials similar to those described with reference to biosensor 10. Biosensor 310, however, is formed to make a photometric measurement of an analyte in a biological fluid.

Cover 312 of biosensor 310 has two spaced apart openings 360, 362 extending between first and second surfaces 48, 50. First opening 360 is positioned adjacent to end 52 and has a first diameter and second opening 362 is positioned adjacent to end 54 and has a second diameter that is less than the first diameter of first opening 360. The first diameter is about 5 mm more preferably about 3 mm and most preferably about 2.5 mm. Second diameter of second opening 262 is about 3 mm, preferably about 2.5 mm, and most preferably about 1.5 mm. It is appreciated that the shapes and sizes of openings 360, 362 can vary in accordance with this disclosure. Additionally, second surface 50 of cover 12 is printed with a circle 364 extending about first opening 360 to serve as an indicator to the user as where to deposit the liquid sample. It is appreciated that cover 312 may be formed without printed circle 364 of that second surface 50 may be printed with a variety of product labeling or instructions for use in accordance with this disclosure.

End 26 of bottom substrate 314 is generally curved in shape as shown in FIG. 10. In addition, first surface 22 of substrate 314 is printed with spaced-apart markings 366 that serve to indicate to a user where to grip biosensor 310 and with an arrow 368 to indicate to a user the direction to slide biosensor 310 into a meter (not shown). Illustratively, markings 366 are shaped as diamonds. It is appreciated, however, that biosensor 310 may be formed without markings and/or arrow, or that markings and/or arrow can be a variety of shapes and sizes and may be appear in a variety of numbers in accordance with this disclosure.

As shown in FIG. 11, cover 312 is coupled to substrate 314 so that sealed portion 336 has an interior border 366 and an exterior border 368. Interior border 366 includes opposite sides 370 that converge from first opening 360 toward second opening 362. Exterior borders 368 are generally linear and lie spaced-apart from edges 56, 58 to form unsealed portions 337 of cover 312. Unsealed portions 337 of cover 12 form gaps (not shown, but which are similar to gas 62, 64 as shown in FIG. 4), between cover 312 and substrate 314. In addition, it is appreciated that the shape and size of borders 366, 368 can vary in accordance with this disclosure.

Opposite sides 370 of interior border cooperates with cover 312 and substrate 314 to define a capillary channel 340 extending between apertures 360, 362. Cover 312, substrate 314, and interior border 366 of sealed portion 36 define channel 340. The converging channel 340 exposes the liquid sample that is applied to biosensor 310 through opening 360 to greater capillary forces as it moves toward reagent 320. Channel 340 has a height similar to that of channel 40 as described above with reference to biosensor 10.

The following example is given for the purpose of illustrating a reagent suitable for use with biosensor 310 that is formed to test cholesterol.

0.117 g methyl hydroxpropylcellulose (Culminal MHPC 8800)

7.000 g titanium dioxide 0.138 g monopotassium dihydrogen phosphate 0.479 g disodium monohydrogen phosphate hydrate 3400 U cholesterol esterase 5000 U cholesterol oxidase $7 \times 10^4$ U peroxidase 0.476 g. sodium dioctyl sulphosuccinate are dissolved in 70 ml. water. There are then successively homogeneously incorporated 14.0 g cellulose 8.4 g polyvinyl propionate dispersion.

Finally, there is added:

0.66 g 3,3',5,5'-tetramethylbenzidine, dissolved in 1.6 ml acetone. This batch is coated in approximately 300 $\mu$ thick layer onto bottom substrate 314. For a further description, see U.S. Pat. No. B1 4,477,575, to Vogel et al. the disclosure of which is expressly incorporated herein by reference. It is appreciated, that any number of photometric reagents may be used with biosensor 310 in accordance with the present invention.

To manufacture biosensor 310 a roll of non-metallized film of substrate material is fed into a slitting station where end 26 is formed to have a curve and into a printing station where markings 366 and arrow 368 are positioned on surface 22. In addition, the substrate material is fed into dispensing and drying station where reagent 320 is compounded and applied in a liquid form to the center of area 78. Rolls of cover material are fed into a slitting and lamination station where openings 360, 362 are punched in cover material. The thermoset adhesive is also applied to one side of the cover material. The other side 50 of cover 312 is marked with circle 364 in printing station. In addition, the adhesive-coated cover material is slit into the appropriate width for each biosensor 10. Next, the adhesive-coated cover material is fed into a sensor assembly station along with the reagent-coated bottom substrate.

In the sensor assembly station, the thermoset adhesive-coated side of the cover material is placed on the substrate material so that second opening 362 is aligned with reagent 320 as shown in FIG. 11. Next, spaced-apart irons (not shown) are placed upon surface 50 of cover material to couple sealed portion 336 to substrate 214. Again, unsealed portions 338, 337 are not exposed to the heat of the iron, and are not coupled to bottom substrate 314. Therefore, channel 340 is formed between cover 312 and substrate 314 and formed to extend between openings 360, 362. Once channel 340 is formed, the assembled material is fed into a sensor cutting and packing station where the material cut to form individual biosensors 310, which are sorted and packed into vials, each closed with a stopper, to give packaged sensor strips.

Although the invention has been described in detail with reference to a preferred embodiment, variations and modifications exist within the scope and spirit of the invention, on as described and defined in the following claims.

What is claimed is:

1. A biosensor comprising:
   a substrate, at least a portion being non-embossed,
   a reagent positioned on the non-embossed portion of the substrate, and
   a cover positioned on the substrate, the cover including a top side and a generally flat non-embossed bottom side, the bottom side being sealed onto the substrate to define a sealed portion having an interior border and an unsealed portion positioned within the interior border of the sealed portion, at least a portion of the unsealed portion of the generally flat non-embossed bottom side cooperating with the substrate to define a channel positioned between the cover and the substrate, having sides defined by the interior border and extending across the reagent.

2. The biosensor of claim 1, wherein the cover includes an opening and the channel extends between the opening and the reagent.

3. The biosensor of claim 2, wherein the cover includes opposite ends and the channel extends between the opening and one of the ends.

4. The biosensor of claim 2, wherein the cover includes a second opening and the channel extends between the first and second openings.

5. The biosensor of claim 4, wherein the cover includes opposite edges and one opening is formed in each of the opposite edges.

6. The biosensor of claim 5, wherein each opening is defined by a disrupted concave surface.

7. The biosensor of claim 2, wherein the cover includes a second opening that is aligned with the reagent.

8. The biosensor of claim 7, wherein the channel converges from the first opening toward the second opening.

9. The biosensor of claim 1, further comprising electrodes positioned on the substrate and the channel extends across at least a portion of the electrodes.

10. The biosensor of claim 9, wherein the cover includes an opening to the channel that is spaced-apart from the electrodes.

11. The biosensor of claim 1, wherein the channel has a height that is less than 10 $\mu$m.

12. The biosensor of claim 1, further comprising an adhesive positioned between the cover and the substrate.

13. The biosensor of claim 1, wherein the cover includes an opening and the channel extends between the opening and the reagent.

14. The biosensor of claim 13, wherein the cover includes a second opening and the channel extends between the first and second openings.

15. The biosensor of claim 14, wherein the channel converges from the first opening toward the second opening.

16. The biosensor of claim 13, wherein the cover includes a second opening that is aligned with the reagent.

17. The biosensor of claim 1, wherein the channel has a height that is less than 10 $\mu$m.

18. The biosensor of claim 1, further comprising an adhesive positioned between the cover and the substrate.

19. A biosensor comprising:

a substrate, at least a portion being non-embossed, a reagent positioned on the non-embossed portion of the substrate, and a cover positioned on the substrate, the cover having a top side and a generally flat non-embossed bottom side, and an opening extending between the top and bottom sides, the bottom side being sealed onto the substrate to define a sealed portion having an interior border and an unsealed portion positioned within the interior border, at least a portion of the unsealed portion of the generally flat non-embossed bottom side cooperating with the substrate to define a channel positioned between the cover and the substrate, having sides defined by the interior border and extending between the opening and the reagent.

20. The biosensor of claim 19, wherein the sealed portion has an interior border that is generally U-shaped.

21. The biosensor of claim 20, further comprising electrodes positioned on the substrate and at least a portion of the electrodes are positioned in the channel.

22. The biosensor of claim 19, wherein the sealed portion has an interior border that converges from the opening toward the reagent.

23. The biosensor of claim 19, wherein the cover includes two openings and the channel extends between the openings.

24. The biosensor of claim 23, wherein the cover includes opposite edges and the openings intersect the edges respectively.

25. The biosensor of claim 23, wherein the substrate includes notches that are aligned with the openings in the cover.

26. The biosensor of claim 23, wherein the sealed portion has an interior border that converges from the first opening toward the second opening.

27. A method of forming a biosensor having a capillary channel, the method comprising the steps of:

providing a substrate, positioning a reagent on the substrate, providing a cover having a top surface and a non-embossed bottom surface, placing a thermoset adhesive on the bottom surface of the cover, placing the adhesive-coated bottom surface on the substrate, and heating portions of the thermoset adhesive to couple the bottom side to the substrate to define a sealed portion having an interior border and an unsealed portion positioned within the interior border, the unsealed portion cooperating with the substrate to define a capillary channel positioned between the cover and the substrate, having sides defined by the interior border and extending across the reagent.

28. The method of claim 27, further comprising the step of placing electrodes on the substrate.

29. The biosensor of claim 28, wherein the cover includes opposite ends and the channel extends between the opening and one of the ends.

30. A biosensor comprising:

a substrate, a reagent positioned on the substrate, a cover positioned on the substrate, the cover including a top side and a bottom side, the bottom side being coupled to the substrate to define a sealed portion having an interior border and an unsealed portion positioned within the interior border, and a non-preformed channel positioned between the unsealed portion of the bottom side and the cover and having sides defined by the interior border, the channel extending across the reagent.

31. The biosensor of claim 30, further comprising electrodes positioned on the substrate and the channel extends across at least a portion of the electrodes.

32. A biosensor comprising:

a substrate, a reagent positioned on the substrate, a cover positioned on the substrate, the cover having a top side and a bottom side, and an opening extending between the top and bottom sides, the bottom side being coupled to the substrate to define a sealed portion having an interior border and an unsealed portion positioned within the interior border, and a non-preformed channel positioned between the unsealed portion of the bottom side and the cover and having sides defined by the interior border, the channel extending between the opening and the reagent.

33. The biosensor of claim 32, wherein the sealed portion has an interior border that is generally U-shaped.

34. The biosensor of claim 33, further comprising electrodes positioned on the substrate and at least a portion of the electrodes are positioned in the channel.

35. The biosensor of claim 32, wherein the sealed portion has an interior border that converges from the opening toward the reagent.

* * * * *